(12) United States Patent
Raber et al.

(10) Patent No.: US 11,597,711 B2
(45) Date of Patent: Mar. 7, 2023

(54) TRANSPARENT GLASSY CANNABINOID COMPOSITIONS

(71) Applicant: Scientific Holdings, LLC, Monrovia, CA (US)

(72) Inventors: Jeffrey Charles Raber, Rancho Palos Verdes, CA (US); Bradley J. Douglass, Seattle, WA (US)

(73) Assignee: Scientific Holdings, LLC, Monrovia, CA (US)

( * ) Notice: Subject to any disclaimer, the term of this patent is extended or adjusted under 35 U.S.C. 154(b) by 0 days.

(21) Appl. No.: 16/849,172

(22) Filed: Apr. 15, 2020

(65) Prior Publication Data

US 2020/0239428 A1     Jul. 30, 2020

Related U.S. Application Data

(63) Continuation of application No. 16/127,150, filed on Sep. 10, 2018, now Pat. No. 10,654,823.

(60) Provisional application No. 62/556,418, filed on Sep. 9, 2017.

(51) Int. Cl.
| | | |
|---|---|---|
| C07D 311/80 | (2006.01) |
| B01D 1/22 | (2006.01) |
| B01D 1/24 | (2006.01) |
| B01D 11/02 | (2006.01) |
| B01D 11/04 | (2006.01) |
| B01D 1/00 | (2006.01) |
| B01F 29/10 | (2022.01) |
| B01F 29/00 | (2022.01) |

(52) U.S. Cl.
CPC ............ *C07D 311/80* (2013.01); *B01D 1/225* (2013.01); *B01D 1/24* (2013.01); *B01D 11/0284* (2013.01); *B01D 11/0488* (2013.01); *B01D 1/007* (2013.01); *B01D 11/0288* (2013.01); *B01D 11/048* (2013.01); *B01D 11/0492* (2013.01); *B01F 29/10* (2022.01); *B01F 29/40* (2022.01)

(58) Field of Classification Search
CPC .................................................. C07D 311/80
USPC ......................................................... 549/385
See application file for complete search history.

(56) References Cited

PUBLICATIONS

Atakan, Therapeutic Advances in Psychopharmacology, (2012) 2(6) 241-254.*
Andre, Front. Plant Sci., 04 2016, 1-17.*

* cited by examiner

*Primary Examiner* — Nizal S Chandrakumar
(74) *Attorney, Agent, or Firm* — Foundation Law Group LLP; JD Harriman

(57) ABSTRACT

The disclosure provides methods and compositions for providing shatter formulations taking the form of crystalline polymorphs, where methods of preparation include preparing tetrahydrocannabinol acid (THCA) powder followed by decarboxylating THCA and removal of terpenes.

4 Claims, 1 Drawing Sheet

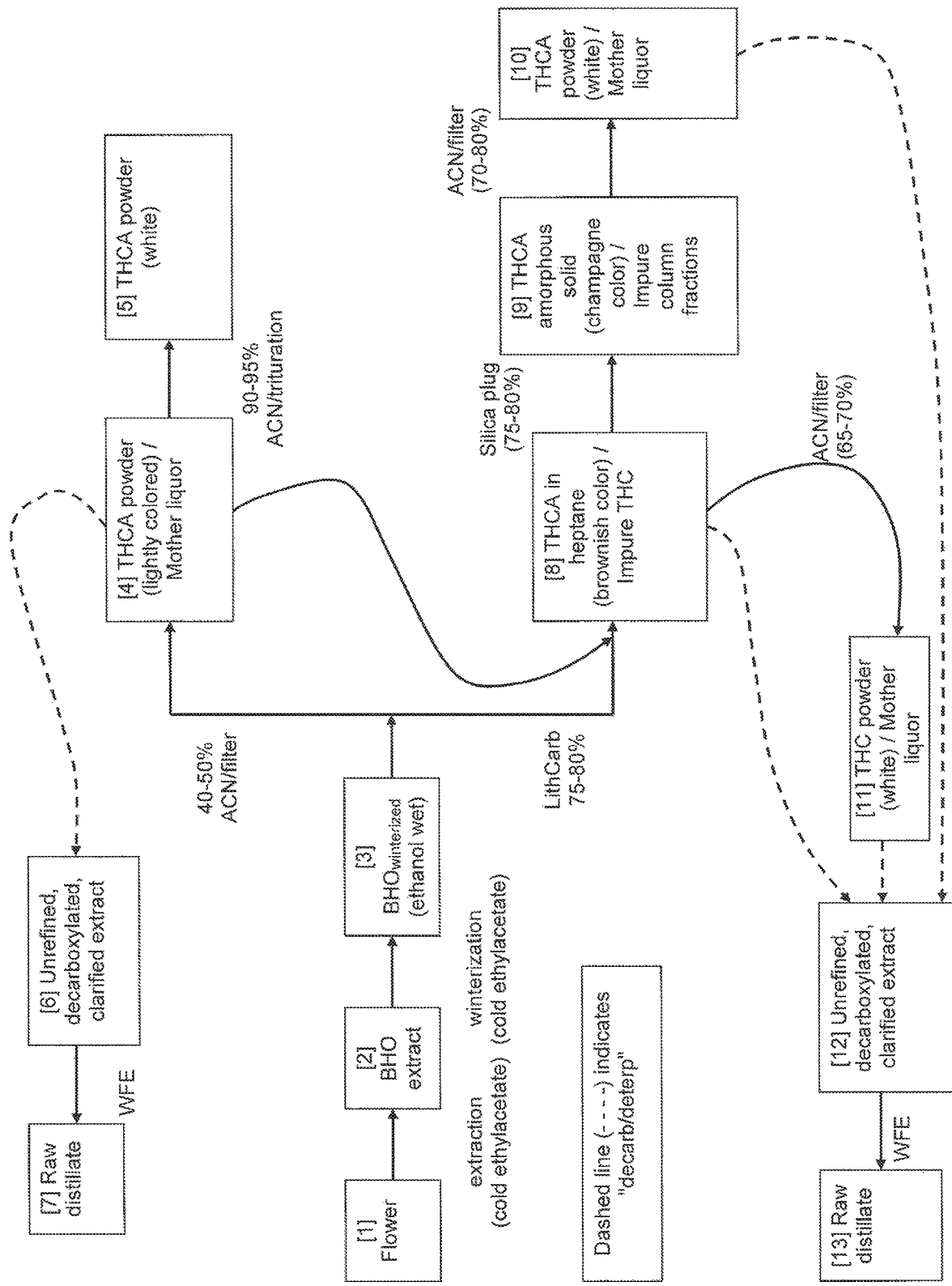

TRANSPARENT GLASSY CANNABINOID COMPOSITIONS

This application claims the benefit of, and priority to U.S. Provisional Patent Application Ser. No. 62/556,418 filed Sep. 9, 2017, and is a continuation of, and claims priority to, U.S. patent application Ser. No. 16/127,150 filed Sep. 10, 2018, the contents of both of which are incorporated herein by reference herein in their entirety.

BACKGROUND OF THE SYSTEM

The cannabinoids from Genus Species include tetrahydrocannabinolic acid (THCA), cannabidiolic acid (CBDA) and cannabigerolic acid (CBGA), tetrahydrocannabinol (CBD), cannabichromene (CBC), cannabigerol (CBG), delta-9-tetrahydrocannabinol (delta-9-THC), and cannabinol (CBN) (see, US 2015/0152018 of Raber et al and US 2015/0080265 of Elzinga et al, each of which is incorporated herein in their entirety, Appendino et al (2008) J. Nat. Prod. 71:1427-1430). Regarding delta-8-THC, an origin of delta-8-tetrahydrocannabinol (delta-8-THC) is described (Owens et al (1981) Clin. Chem. 27:619-624). The present disclosure provides new formulations and products comprising cannabinoids and terpenes, can encompass unique crystalline polymorphs, and where the products made from the formulations can have a consistency ranging from brittle to taffy-like.

SUMMARY

Briefly stated, the present disclosure provides a mortar and pestle method that provides a formulation from an amorphous THCA powder. Also provided are compositions made by that method. Also provided is a DAC method that provides a formulation from an amorphous THCA powder. Compositions made by that method are also provided. In addition, are methods that provide formulations from a crystalline THCA powder. What is provided is a solution-phase, pre-formulation that provides a formulation form a crystalline THCA powder. Compositions made from this method are also provided. Moreover, what is provided is solid phase pre-formulation and syringe pump method that provides formulation from crystallizing THCA powder. Compositions from this method are also provided.

BRIEF DESCRIPTION OF THE DRAWINGS

FIG. 1. Flow chart with steps including extraction, winterization, filtering, and decarboxylation.

DETAILED DESCRIPTION OF THE SYSTEM

As used herein, including the appended claims, the singular forms of words such as "a," "an," and "the" include their corresponding plural references unless the context clearly dictates otherwise. All references cited herein are incorporated by reference to the same extent as if each individual patent, and published patent application, as well as figures, drawings, sequence listings, compact discs, and the like, was specifically and individually indicated to be incorporated by reference.

Identifying Polymorphs

Compositions of the present disclosure, including polymorphs, can be characterized by Differential Scanning calorimetry (DSC), Fourier Transform Infrared Spectroscopy (FTIR), Fourier Transform Near-Infrared Spectroscopy (NIR), Powder X-Ray Diffraction (PXRD), Thermal Gravimetric Analysis (TGA), Solid State Nuclear Magnetic Resonance (SSNMR). Additional methods include atomic absorption spectroscopy, titrimetric assays, raman spectra, and ion chromatography.

U.S. Pat. No. 7,091,246, which is incorporated, herein in its entirety, provides the following account of how scanning calorimetry is used. Differential Scanning calorimetry (DSC) measures heat now as a function of time or temperature and is used to study material transformation whether they be physical, such as phase changes, or chemical, such as decomposition. Parameters that can he obtained from a DSC thermogram include, onset temperature, the temperature of the peak minimum, and the peak width. DSC provides information on purity. For example, when a pure crystalline substance melts, the melting point is sharp. In DSC, that sharpness is shown by a narrow melting peak in the thermogram. If there are impurities or defects in the crystalline nature, the melting takes place at lower temperatures and over a larger range of temperatures. In DSC, the impurities are shown by a lower onset temperature and peak temperature, and a broader peak in the thermogram. When there are discrete impurities, they can melt at their melting points. In DSC, discrete impurities can be shown by additional peaks in the thermogram. Decomposition may be a parameter of interest, when characterizing polymorphs. While a decomposition curve is usually broader and can be more complicated, some of the same phenomena are seen as with melting. Impurities and defects will cause broader and lower temperature peaks. Discrete impurities can show their own decomposition peaks.

A solid material that can exist as two or more polymorphs can be characterized according to whether it is enantiotropic or monotropic. Solid phase transitions that transform reversibly without passing through the liquid or gas phase are enantiotropic transitions. But where the polymorphs are not convertible without passing through liquid or gas phase, the system is monotropic and the transition, when it occurs, is a monotropic transition (see, Carletta et al (2015) Solid-state investigation of polymorphism and tautomerism of phenylthiazole-thione; a combined crystallographic, calorimetric and theoretical survey. Cryst. Growth Des. 15:2461-2473).

The present disclosure encompasses methods for creating different polymorphic forms, or for creating different ratios of various polymorphic forms. These methods include solvent effects, for example, where the packing of a crystal can differ in polar versus in nonpolar solvents. These methods include adding an impurity that inhibit growth patterns and favors the growth of a metastable polymorph. Another method, is altering the level of supersaturation from which material is crystallized (the higher the concentration above the solubility, the more likely is metastable formation). Other parameters that can be varied, are temperature used during crystallization, and degree of stirring.

Cannabinoids

One of more of the following cannabinoids can be included in the compositions of the present disclosure. Alternatively, one of more of the following cannabinoids can be excluded (omitted) from the compositions and methods of the present disclosure. Cannaboids and related compounds include, for example, cannabigerol; cannabichromene; cannabitriol; cannabidiol; cannabicyclolol; cannabielsoin; cannabinodiol; cannabinol; delta-8-tetrahydrocannabinol; delta-9-tetrahydrocannabinol; cannabichromanone; cannabicoumaronone; cannabicitran; 10-oxo-delta-6a10a-tetrahydrocannabinol; cannabiglendol;

delta-7-isotetrahydrocannabinol; CBLVA; CBV; CBEVA-B; CBCVA; delta-9-THCVA; CBDVA; CBGVA; divarinolic acid; quercetin; kaemferol; dihydrokaempferol; dihydroquercetin; cannflavin B; isovitexin; apigenin; naringenin; eriodictyol; luteolin; orientin; cytisoside; vitexin; canniprene; 3,4'-dihydroxy-5-methoxy bibenzyl; dihydroresveratrol; 3,4'-dihydroxy-5,3dimethoxy-5'-isoprenyl; cannabistilbene 1; cannabistilbene 11a; cannabistilbene 11b; cannithrene 1; cannithrene 2; cannabispirone; iso-cannabispirone; cannabispirenone-A; cannabispirenone-B; cannabispiradienone; alpha-cannabispiranol; beta-cannabispiranol; acetyl-cannabispirol; 7-hydroxy-5-methoxyindan-1-spiro-cyclohexane; 5-hydroxy-7-methoxyindan-1-spiro cyclohexane; myristic acid, palmitic acid, oleic acid, stearic acid, linoleic acid, linolenic acid, arachidic acid, eicosenoic acid, behenic acid, lignoceric acid, 5,7-dihydroxyindan-1-cyclohexane; cannabispiradienone; 3,4'-dihydroxy-5-methoxybibenzyl; canniprene; cannabispirone; cannithrene 1; cannithrene 2; alpha-cannabispiranol; acetyl-cannabispirol; vomifoliol; dihydrovomifoliol; beta-ionone; dihydroactinidiolide; palustrine; palustridine; plus-cannabisativine; anhydrocannabisativine; dihydroperiphylline; cannabisin-A; cannabisin-B; cannabisin-C; cannabisin-D; grossamide; cannabisin-E; cannabisin-F; cannabisin-G; and so on (see, e.g., Flores-Sanchez and Verpoorte (2008) Secondary metabolism in cannabis in Phytochem. Rev. DOI 10.1007/s11101-008-9094-4). Suppliers of tetrahydrocannabinolic acid (THCA) and other cannabinoids include Sigma-Aldrich, St. Louis, Mo. and Echo Pharmaceuticals, Rijnkade 17B, The Netherlands.

Measuring Cannabinoids

Cannabinoids can be separated, purified, analyzed, acid quantified by a number of techniques. Available equipment and methods include, gas chromatography, HPLC (high pressure liquid chromatography, high performance liquid chromatography), mass spectrometry, time-of-flight mass spectrometry, gas chromatography-mass spectrometry (GC-MS), and liquid chromatography-mass spectrometry (LC-MS). Equipment for separation and analysis is available from Waters Corp., Milford, Mass.; Agilent, Foster City, Calif.; Applied Biosystems, Foster City, Calif.; and Bio-Rad Corp., Hercules, Calif.

The present disclosure provides in-line monitoring, of purification, that is, quantitation THC as well as quantitation of impurities. In-line monitoring may be by UPLC methods, or by other methods. Ultra-high performance liquid chromatography (UPLC) is similar to HPLC, except that UPLC uses smaller particles in the column bed, and greater pressures. The particles can be under 2 micrometers in diameter, and pressures can be nearly 15,000 psi. UPLC also uses higher flow rates, and can provide superior resolution and run times in the range of under 30 seconds (Wren and Tchelitcheff (2006) J. Chromatography A. 1119:140-146; Swartz, M. E. (May 2005) Separation Science Redefined). The application of UPLC to cannabinoids has been described (see, Jamey et al (2008) J. Analytical Toxicology. 32:349-354; Badawi et al (2009) Clinical Chemistry. 55:2004-2018). Suitable UPLC columns for cannabinoid analysis include, e.g., Acquity.®. UPLC HSS T3 C18, and Acquity.®. UPLC BEH C18 column (Waters, Milford, Mass.). Other methods for detecting cannabinoids include, e.g., infrared (IR) spectroscopy, gas chromatography mass spectroscopy (GCMS), and electrospray tandem mass spectroscopy (ESI-MS/MS) (Ernst et al (2012) Forensic Sci. Int. 222:216-222). Biochemical properties of terpenes, including receptor binding, can be assessed using labeled terpenes and labeled ligands where a terpene influences binding properties of the labeled ligand. Useful labels include radioactive labels, epitope tags, fluorescent dyes, electron-dense reagents, substrates, or enzymes, e.g., as used in enzyme-linked immunoassays, or fluorenes (see, e.g., Rozinov and Nolan (1998) Chem. Biol. 5:713-728).

Terpenes

The present disclosure provides terpenes, either endogenous or exogenous (intentionally added), as a component of a cannabinoid composition.

Berry GDP (Berry Granddaddy Purple) blend ingredients include the following. The top ten in descending order of prominence are: beta-myrcene, beta-caryophyllene, alpha-pinene, linalool, valencene, alpha-humulene, beta-ocimene, beta-pinene, D-limonene, and alpha-bisabolol. Provided is composition that contains only these terpenes (consists of only these terpenes). Also, provided is a composition that comprises these terpenes.

Pineapple Super Silver Haze blend ingredients include the following. Top ten components in descending order of prominence: Terpinolene, beta-myrcene, beta-ocimene, D-limonene, beta-caryophyllene, beta-pinene, alpha-pinene, alpha-phellandrene, alpha-humulene, and alpha-terpinene. Provided is composition that contains only these terpenes (consists of only these terpenes). Also, provided is a composition that comprises these terpenes.

Tropical Trainwreck is a terpene blend that contains these top 10 in descending order of prominence: Terpinolene, beta-caryophyllene, D-limonene, beta-myrcene, beta-pinene, ocimene, alpha-pinene, valencene, alpha-humulene, terpineol. Provided is composition that contains only these terpenes (consists of only these terpenes). Also, provided is a composition that comprises these terpenes.

Some examples of terpenes, and their classification, are as follows:

Hemiterpenes: Examples of hemiterpenes, which do not necessarily have an odor, are 2-methyl-1,3-butadiene, hemialboside, and hymenoside;

Monoterpenes: pinene; alpha-pinene, beta-pinene, cis-pinane, trans-pinane, cis-pinanol, trans-pinanol (Erman and Kane (2008) Chem. Biodivers. 5:910-919), limonene; linalool; myrcene; eucalyptol; alpha-phellandrene; beta-phellandrene; alpha-ocimene; beta-ocimene, cis-ocimene, ocimene, delta-3-carene; fenchol; sabinene, borneol, isoborneol, camphene, camphor, phellandrene, alpha-phellandrene, alpha-terpinene, geraniol, linalool, nerol, menthol, myrcene, terpinolene, alpha-terpinolene, beta-terpinolene, gamma-terpinolene, delta-terpinolene, alpha-terpineol, trans-2-pinanol, Sesquiterpenes: caryophyllene; beta-caryophyllene, caryophyllene oxide, humulene, alpha-humulene, alpha-bisabolene; beta-bisabolene; santalol; selinene; nerolidol, bisabolol; alpha-cedrene, beta-cedrene, beta-eudesmol, eudesm-7(11)-en-4-ol, selina-3,7(11)-diene, guaiol, valencene, alpha-guaiene, beta-guaiene, delta-guaiene, guaiene, farnesene, alpha-farnesene, beta-farnesene, elemene, alpha-elemene, beta-elemene, gamma-elemene, delta-elemene, germacrene, germacrene A, germacrene B, germacrene C, germacrene D, germacrene E.

Diterpenes: oridonin, Triterpenes: ursolic acid; oleanolic acid; "1.5 ene"; guaia-1(10), 11-diene can be characterized as a 1.5 ene. Guaia-1(10),11-diene is halfway between a monoterpene and diterpene, in terms of how many isoprenoid units are present. Monoterpene is $C_{10}H_{16}$, and diterpene is $C_{20}H_{32}$. Guaia-1(10), 11-diene is $C_{15}H_{24}$. Isoprene is $C_5H_8$ (two double bonds).

Terpene formulations of the present disclosure may comprise one or more selected from a list comprising alpha-bisabolol, borneol, camphene, camphor, beta-caryophyllene, delta-3-carene, caryophyllene oxide, alpha-cedrene, beta-eudesmol, fenchol, geraniol, guaiol, alpha-humulene, isoborneol, limonene, linalool, menthol, myrcene, nerol, cis-ocimene, trans-ocimene, alpha-phellandrene, alpha-pinene, beta-pinene, sabinene, alpha-terpinene, alpha-terpineol, terpinolene, alpha-guaiene, elemene, farnesene, germacrene B, guaia-1(10), 11-diene, trans-2-pinanol, selina-3,7(11)-diene, eudesm-7(11)-en-4-ol, and valencene. See, US 2015/0080265 of Elzinga et al, which discloses these and other terpenes and terpene formulations, ranges, terpene combinations, exclusionary embodiments, suppliers of chemicals, human subject sensory panels, and the like, all of which are incorporated herein by reference.

Terpenes modify and modulate the effects of THC and other cannabinoids and impact the overall medicinal properties of the particular cultivar. Physiological effects can be detected when inhaled from ambient air, where the result is serum levels in the single digit mg/mL range (see, US 2015/0080265 of Elzinga and Raber, which is incorporated herein by reference in its entirety). Terpenes display unique therapeutic effects that may contribute to the overall effects of medicinal cannabis. The synergy of terpenes and cannabinoids are likely responsible for providing the effective treatment of pain, anxiety, epilepsy, inflammation, depression, and infections (McPartland and Russo (2001) J. Cannabis Ther. 1:103-132).

The term "entourage effect" refers to the influence of the combination of cannabinoids and terpenes that results in synergic effects on physiology (Russo (2011) Brit. J. Pharmacol. 163:1344-1364; Corral (2001) J. Cannabis Therapeutics. vol. 1, issue 3-4). Terpenes in cannabis have been described. See, Flores-Sanchez and Verpoorte (2008) Phytochem. Rev. 7:615-639, and US2015/0080265 of Elzinga and Raber and US2015/0152018 of Raber and Elzinga, each of which is incorporated herein in its entirety.

This describes butane hash oil (BHO). Butane hash oil is a high-potency cannabis concentrate that has much higher THC content than flower cannabis. See, Miller et al (2016) J. Psychoactive Drugs. 48:44-49; Chan et al (2017) Drug Alcohol Depend. 178:32-38; Meier M H (2017) Drug Alcohol Depend. 179:25-31.

Butane hash oil (BHO) is a concentrate or extract derived from plant material, utilizing n-butane or a similar light alkane to perform the extraction process, where the extraction solvent is easily removed, following the extraction procedure. Solvent-based extraction is where plant matter containing extractable compounds is bathed or washed in a solvent. The extractable compounds from the plant material dissolve in the solvent. The solution is then purified to remove the solvent and recover the desired extracted compounds. Optionally, the purification process involves beating the solution to boil off or volatilize the solvent from the solution, leaving the extracted compounds behind. Such extraction methods use a solvent having a lower boiling point than the boiling points of the products, and in this way, the solvent can be removed without removing the extracted compounds with minimizing heat-induced damage to the extracted compounds. U.S. Pat. No. 9,327,210 of Jones describes method to prepare butane hash oil (BHO). Process of extracting hash oil from cannabis plant material often involves running butane, a hydrocarbon-based solvent, through the plant material or soaking the plant material in butane to wash out the cannabinoids. The cannabinoid-rich solvent solution is then purified, often by heating it, which volatilizes the butane and leaves behind the cannabinoid extract (see, U.S. Pat. No. 9,327,210 of Jones, which is incorporated herein by reference in its entirety). Butane is preferably a food-grade, refined n-butane or isobutane.

Decarboxylation of THCA

THCA compounds can be decarboxylated. For example, Dussy et al achieved a 70% yield with treatment of a dry THCA compounds at 150 degrees C. (see, Dussy et al (2005) Isolation of Delta-9-THCA-A from hemp and analytical aspects concerning the determination of Delta9-THC in cannabis products. 149:3-10). Drying was with nitrogen gas. Decarboxylation can be, for example, under the condition of 80 degrees, 95 degrees C., 110 degrees C., 130 degrees C., 145 degrees C., 150 degrees C., 175 degrees C., 200 degrees C., 225 degrees C. and like. Drying can be for various times up to 60 minutes, or up to 90 minutes, or up to 120 minutes, and so on. Drying can be in the dried state under nitrogen gas, or in a dried state under atmospheric air, or as dissolved in a solvent such as methanol, acetonitrile, or tetrahydroforan, as an emulsion in water, or suspended in a non-ionic detergent in water, or suspended in an ionic detergent in water.

Wiped Film Evaporation

Wiped film evaporation has been described by one supplier, LCI Corp, Charlotte, N.C. Without implying any limitation on the present disclosure, LCI Corp.'s description is, "The agitated thin film evaporator, commonly referred to as a "wiped film evaporator," consists of two major assemblies: a cylindrical heated body and a rotor. Product is introduced above the heated zone and is evenly distributed over the evaporator's inner surface by the rotor. As the product spirals down the wall, the high rotor tip speed generates highly turbulent flow resulting in the formation of bow waves and creating optimum heat flax and mass transfer conditions.

Volatile components are rapidly evaporated via conductive heat transfer. Vapors flow either counter-currently or co-currently through the unit, depending on the application requirements. In both cases, vapors are ready for condensing or subsequent processing, that is, fractionation, after exiting the vapor discharge section.

Nonvolatile components are discharged at the outlet. Continuous agitation and mixing by the rotor blades minimizes fouling of the thermal wall where the product or residue is most concentrated. The combination of 1) extremely short residence time, 2) narrow residence time distribution, 3) high turbulence, and 4) rapid surface renewal permits the thin film evaporator to successfully handle heat-sensitive, viscous and fouling-type fluids."

A description of wiped film evaporation from another supplier, Pope Scientific, Saukville, Wis., reads, "Short Path/Wiped-Film Stills (WFS) and Wiped-Film Evaporators (WFE) successfully separate volatile from less volatile components for Oils, Fats, Chemicals, Polymers, Nutraceuticals, Fragrances, with a gentle process utilizing the thin-film wiping action of feed liquid through a heated cylindrical vacuum chamber with high vacuum (vacuum distillation/evaporation). Keys to the superiority of this process include: Short residence time of the feed liquid, Significantly lowered temperature due to high vacuum capability, and Optimal efficiency in mass and heat transfer. The brief (seconds) exposure of feed liquid to heated walls is due in part to the slotted wiper design which forces the liquid downward with strict control of residence time, film thickness, and flow characteristics."

Dual Asymmetric Centrifugal Mixing

DAC cup is a high shear mixer used in the THC coating method of salts and sugars, as applied to the compositions and methods of the present disclosure. DAC cup is Dual Asymmetric Centrifugal mixing unit.

One supplier of Dual Asymmetric Centrifuge (FlackTek, Inc. Landrum, S.C.) describes DAC as, "The SpeedMixer DAC 10000 HP works by the spinning of a high speed mixing arm in one direction while the basket rotates in the opposite direction, thus, the name Dual Asymmetric Centrifuge. This combination of forces in different planes enables incredibly fast mixing, and yet the precision construction of each machine gives it a balance that allows amazingly quiet operation.

With this instrument, the typical mixing time for fully dispersing a colour paste in a silicone sealant is less than 10 seconds; for mixing fumed silica or precipitated chalk silicone formulations 8-14 seconds will normally suffice. These are both operations that would otherwise require up to 3 hours or more of mixing time, and they can only be done in quantities of 1 quart or greater. Mixing does not incorporate any air and additional mixing time removes air from the blend, yielding a finished product when the mixing process is done. Fluids of widely differing viscosities can be blended quickly.

Rheometers for Measuring Consistency of Resin, Taffy-Like Substances, and Liquids Consistency of the compositions of the present disclosure, in terms of viscosity of resins and of taffy-like substances, can be measured with a rheometer. Torque rheometers are available (see, Brabender Plastigraph, Brabender GmbH, Duisburg, Germany; Haake Rheocord, Thermo Electron Corp. Newington, N.H.). These can take measurements on plastic resins, for example. Viscosity of substances with a taffy-like consistency, as well as of waxes and liquids, can be measured with TA Instruments AR2000 rheometer (TA Instruments, New Castle, Del.) and Brookfield DVIII rheometer (Brookfield Engineering Laboratories, Middleboro, Mass.).

Polymorphs of the Present Disclosure

The present disclosure provides polymorphs that arise from using different salts, that is, one type of salt causing the composition to assume a first polymorph and a second type of salt causing the composition to assume a second polymorph. Moreover, the disclosure provides polymorphs arising from using a different counterion, that is, changing only the anion component of a salt, where the result is either a first polymorph or a second polymorph. Additionally, what is provided is polymorphs arising from using a different counterion, involving changing the cation counterion of the salt, resulting in either a first polymorph or, a second polymorph. Polymorphs of the present disclosure can be produced by solvent effects, intentionally added impurities, level of supersaturation from which material is crystallized, temperature at which crystallization occurs, stirring conditions, and so on, or any combination of the above. Physical properties can define the compositions of the present disclosure, including inciting point, stability to decarboxylation, and other properties, characteristics, and parameters as disclosed, for example, by Soda (U.S. Pat. No. 9,499,543, Okumura (WO2014/104414), and Rushforth (U.S. Pat. No. 7,091,246). For example, melting point of commercially available THCA is 78-88 degrees C.

DETAILED DESCRIPTION OF THE FIGURES

FIG. 1. This provides a flow chart showing the steps of extraction and winterization, which are carried out in cold ethylacetate. The very first step in the flow chart is extraction. A preferred solvent is n-butane in this extraction procedure. However, any light hydrocarbon, such as, propane, methylbutane tetrafluoroethane, is expected also to work for purposes of this type of extraction. The winterized product (BHOwinterized) can then be subjected to either 40-50% ACN/filtering or to LithCarb 75-80%. BHO means Butane Hash Oil. LithCarb means lithium carbonate ($Li_2CO_3$). Carbonate is the base used to basify the THCA to make it soluble in water. Lithium is the counterion that may have an additional effect of creating the polymorph/salt. Lithium carbonate is critical to this process because it works where other commonly used carbonate bases, such as sodium carbonate, do not. Along with the use of acetonitrile (ACN) as solvent, the use of lithium carbonate is a unique and novel step because it enables this process and the resulting composition of matter. One advantage of LithCarb path is elimination of all known pesticides. Also, the acetonitrile (ACN) step provides the advantage of removing some or all pesticides.

Pesticide-free embodiments are provided. The methods, procedures, and compositons of the present disclosure can be substantially pesticide-free. This can refer to all pesticides (natural as well as synthetic), naturally occurring pesticides, or synthetic pesticides. In embodiments, the pesticide level can be in terms of weight in a THCA powder, weight in a raw distillate, weight in a hard, sticky paste, and so on. Also, the pesticide level can be in terms of weight of pesticide in a kilogram of dried plant matter, weight of pesticide in a kilogram of "wet" plant matter is it occurs at the time of being harvested, in terms of total pesticides, or in terms of an individual pesticide, or in terms of a combination of any two, any three, any four, or any five pesticides. A number of pesticides are named below.

The pesticide weight can be under 10 picograms (pg)/kg, under 20 pg/kg, under 40 pg/kg, under 60 pg/kg, under 100 pg/kg, under 200 pg/kg, under 400 pg/kg, under 800 pg/kg, under 1000 pg/kg, under 10 nanograms (ng)/kg, under 20 ng/kg, under 40 ng/kg, under 60 ng/kg, under 80 ng/kg under 100 ng/kg, under 200 ng/kg, under 400 ng/kg, under 600 ng/kg, under 800 ng/kg, under 1 micrograms/kg, under 2 micrograms/kg, under 4 micrograms/kg, under 6 micrograms/kg, under 8 micrograms/kg, under 10 micrograms/kg, under 20 micrograms/kg, under 40 micrograms/kg, under 60 micrograms/kg, under 80 micrograms/kg, under 100 micrograms/kg, under 0.2 mg/kg, under 0.4 mg/kg, under 0.6 mg/kg, under 0.8 mg/kg, under 1.0 mg/kg, under 2 mg/kg, under 4 mg/kg, under 6 mg/kg, under 8 mg/kg, under 10 mg/kg, under 20 mg/kg, under 40 mg/kg, under 60 mg/kg, under 80 mg/kg, under 100 mg/kg, under 200 mg/kg, under 400 mg/kg, under 600 mg/kg, under 800 mg/kg, under 1,000 mg/kg, and so on.

Pesticides include, Aldicarb, Abamectin, Azoxystrobin, Bifenazate, Boscalid, Bifenazate, Bifenthrin, Carbaryl, Cypermetrin, Cyflutrin, Chlofenapyr, Chlorpyrifos, Captan, Dimethomorph, Diazinon, Diaminozide, Etoxazole, Fenhexamide, Fenoxycarb, Fenpyroximate, Flonicamid, Fludooxonil, Hexythiazox, Imidacloprid, Myclobutanil, Malathion, Paclobutrazole (Bonzi), Piperonyl butoxide, Pyrethrins, Propiconazole, Permetrin, Spinosad, Spinetoram, Spirotetramat, Spiromesifen, Tebuconazole, Thiamethoxam, Trifloxystrobin.

Winterization is a cannabinoid purification process in which a crude cannabis extract is subjected to a solvent, typically ethanol, that dissolves the cannabinoids but causes fats and waxes to precipitate. The solid fats and waxes are then separated from the solution of purified cannabinoids via filtration.

In the flowchart of FIG. 1, the steps near the top show the conversion of BHOwinterized to a white THCA powder. In the flow chart, the steps shown near the bottom also show the conversion of BHOwinterized to white THCA powder. For both the upper series of steps and for the lower series of steps, branch points can occur where the composition is subjected to decarboxylation/deterpenization. Deterpenation means removal of terpenes. The conditions for decarboxylation/deterpenation are, Temperature: 130 degrees C., Pressure: 0.1 Torr, Time: 2 hour.

The lower series of steps shows use of silica plug. A silica "plug" is a small quantity of silica gel that the solution of THCA in heptane is filtered through. Silica gel and glass are both composed of silicon dioxide. Silica gel differs in that it is silicon dioxide in powder form with a very small particle size as compared, for example, to sand. The upper series of steps and the lower series of steps show filtration steps. "Filter" denotes the operation of filtration rather than the use of a filter. Multiple types of filters can be used in this process and the pore size is not critical.

The final step of the flow chart, which are shown at the far left (bottom), and which occurs immediately after the decarboxylation/deterpenation step, is the wiped film evaporation (WFE) step.

Narrative for the Flow Chart Boxes of FIG. 1

Mother liquor. Mother liquor is shown in flow chart boxes 4, 10, and 11. Mother liquor is the remaining acetonitrile solution of winterized BHO. This solution contains some THCA in it because THCA is sparingly soluble in acetonitrile. In these flow chart boxes, the THCA powder is left sitting on top of the filter, while the mother liquor has passed through the filter.

Yields. Yields are shown for various steps, that is, in the transition from a given box to the next box. Yields were determined to be 40-50% (Box 3 to Box 4), 90-95% (Box 4 to Box 5), 75-80% (Box 3 to Box 8), 75-80% (Box 8 to Box 9), and 70-80% (Box 9 to Box 10). A relatively low yield, such as 40-50%, may be due to some of the THCA still dissolved in the acetonitrile mother liquor, and where only a portion of the THCA precipitates as a white powder.

Processing pathways. The flow chart boxes of FIG. 1 illustrate various processing pathways, such as that beginning with Box 1 (flower) and ending at Box 10 (THCA powder), or beginning with Box 1 (flower), continuing to Box 10 (THCA powder), and continuing through decarboxylation/deterpenation step and then wiped film evaporator (WFE) step, and concluding at Box 13 (raw distillate). The dashed line in the flow chart indicates decarboxylation/deterpenation step. As shown immediately below, the advantages of one or more of the indicated flow chart processing pathways can be the isolation of high purity THCA with a simple solvent extraction, or the production of a product that is clearer and less colored, or the production of a product with a greater yield.

(A) Boxes 1, 2, 3, 4, 5. Advantage: Allows the isolation of high purity THCA with a simple solvent extraction. Disadvantage: Low yield (B) Boxes 1, 2, 3, 4, 6, 7. Advantage: Allows the isolation of high purity THC with a simple solvent extraction followed by decarboxylation and WFE. Disadvantage: same as (A)

(C) Boxes 1, 2, 3, 4, 8, 12, 13. Advantage: Same as (B). Disadvantage: same as (A)

(D) Boxes 1, 2, 3, 4, 8, 11, 12, 13. Advantage: Produces a clearer (i.e. more colorless product) compared to (C). Disadvantage: Lower yield than (C)

(E) Boxes 1, 2, 3, 8, 12, 13. Advantage: Similar to (C) but higher yield (F) Boxes 1, 2, 3, 8, 11, 12, 13. Advantage: Similar to (D) but higher yield (G) Boxes 1, 2, 3, 8, 9, 10, 12, 13. Advantage: Similar to (F) but produces a clearer (i.e. more colorless product) compared to (F)

(H) Boxes 1, 2, 3, 8, 9, 10. Advantage: Similar to 1, 2, 3, 4 [Like e pathway in (A)] but higher yielding.

Raw distillate. This concerns "raw distillate." Anywhere that "raw distillate" is required in a procedure to make one or more embodiments of the present disclosure, the products denoted by Block 12 or by Block 13 can be used. Raw distillate is not an integral ingredient in Protoshatter of the present disclosure, that is, it is the ease that some embodiments of Protoshatter include raw distillate, while other embodiments do not include raw distillate.

As shown by the flow chart of FIG. 1, "raw distillate" is the result of procedures that include decarboxylation/deterpenization. Applicants have routinely conducted quantitative chemical conversion and routinely reached yields of 100%. Tn embodiments, the present disclosure encompasses compositions and methods, where decarboxyation is at least 50%, at least 60%, at least 70%, at least 80%, at least90%, at least 95%, at least 99%, and so on. Also, the present disclosure encompasses compositions and methods, where decarboxyation is about 50%, about 60%, about 70%, about 80%, about 90%, about 95%, about 99%, and so on.

THCA powder. THCA powder is a required component is required by all four of these methods of the present disclosure: (1) Mortar and Pestle Method; (2) DAC Method; (3) Solution-Phase Pre-Formulation; and (4) Solid Phase Preformulation and Syringe Pump Method. As shown in the flow chart of FIG. 1, THCA powder is produce in blocks 4, 5, 9, 10, and 11. THCA powder that is produced by the previous steps that terminate in any of these blocks can be used for making Protoshatter. What is preferred for making Protoshatter, is the THCA powder from blocks 5, 10, and 11, because these THCA powders are colorless (a desired attribute).

EXAMPLES

Example 1

Procedures of the present disclosure provided a composition that may be a form of a lithium salt that is not a crystal polymorph or, alternatively, a crystal polymorph. Elemental analysis or 2D NMR may distinguish between these two possibilities. Also, procedures of the present disclosure provided a THCA composition that is different from commercially available THCA, where the THCA composition was distinguished from commercially available THCA by melting point, and where the different melting points indicated two different polymorphs (the present THCA versus commercially available THCA). THCA composition prepared by methods of the present disclosure was found to be more difficult to carboxylate than commercially available THCA, providing evidence for a unique polymorph.

Example 2

Methods of the present disclosure generated a crystal polymorph that appears to he the result of solvent effects caused by the acetonitrile. Melting point of THCA polymorph/salt of the present disclosure is, 137-142 degrees C. Stability to decarboxylation of a typical THCA rich extract is moderate, while stability of THCA polymorph/salt of the present disclosure is resistant.

Process for Producing Protoshatter using TWS THCA salt/polymorph: Advantages of the present disclosure over Standard Shatter Process include: (1) Formulated from purified, discrete feedstocks (bottom-up); (2) Standard shatter depends on quality of plant material and characteristics (top-down); (3) Control over flavor characteristics; (4) Standard shatter is limited by plant material only; (5) Formulated with purified THC and terpene blends to create amorphous, glass state; (6) Standard shatter process is limited by characteristics of the plant; (7) Does not require gaseous, hydrocarbon extraction step; (8) Enables scale-up and potentially continuous process automation; (9) Standard shatter is limited to batch-wise production and small batch sizes.

Protoshatter Formulas ("a." is the preferred formula); Preferred Ratio of Ingredients (ideal mass ratio); THC & Terpenes Formula; THCA:THC:Terpenes 11:2:1.5; Plus Phytol Formula; THCA: THC: Terpenes:Phytol 11:1:1.5: 0.5.

Preferred Range of Ingredients (weight % range); THC & Terpenes Formula; THCA=70-80%; THC=10-15%; Terpenes=5-10%; Plus Phytol Formula; THCA=70-80%; THC=5-8%; Terpenes=5-10%; Phytol=2-4%.

Protoshatter Laboratory Procedures

Protoshatter has nearly identical physical qualities to a high-value concentrate product called shatter. It is a transparent glass, often lightly colored with yellow, amber, or red tones. Its consistency ranges from brittle to taffy-like. Protoshatter is made by combination of high purity THCA powder (85-100% THCA by mass, HPLC), raw cannabis distillate (75%-90% THC by mass, HPLC) and terpenes (typically 4-10%). Typical acid purity used is 93% THCA and greater. It is conceivable that acid as low as 70% might be used without addition of raw distillate. Typical distillate purity is 85% THC. We do have evidence that distillate purity impacts the formulation process or the consistency of the final product.

The remainder of the mass fraction in THCA powder and distillate is largely other cannabinoids. Most simply, the constituents are mixed and melted together to yield the product.

Raw distillate is incorporated into the product to facilitate formulation, control consistency and improve shelf-stability. The product ranges in consistency from a brittle glass to a semi-liquid, taffy-like state. We have found that this quality is a function of the fraction of acidic cannabinoid components (predominantly THCA), where the addition of raw distillate or terpenes results in a decreasingly brittle product. The addition of distillate lowers the apparent melting point of the product, allowing for more facile manipulations and formulation.

Shelf-stability is worsened by high purity of acid or truly crystalline THCA starting materials. Products made with these inputs are prone to 'sugaring'—a crystallization process forming a form of 'sugar wax' or protosugar—during either formulation (spontaneous, on heating) or on standing over time. While typically undesired during protoshatter formulation, sugar is also a very high value product and methods for its production should be protected as well.

This crystallization process requires a measure of liquidity to the product, so very brittle products may require heating to sugar and not prone to sugaring at room temperature. Despite a lower purity, products trending towards a liquid state are also prone to sugar, especially as terpenes evaporate.

As a result, methods for the formulation of protoshatter differ depending on the purity and polymorphism of the input THCA material. THCA powder crystallized from acetonitrile (MeCN) requires greater temperatures to formulate to protoshatter, and is prone to sugaring during this process. Amorphous, non-crystalline THCA powder requires less heating to formulate and mixes more easily with terpenes.

The following are some example experimentals for the formulation of protoshatter by different means.

Formulation from Amorphous THCA Powder

Mortar and Pestle Method. To a mortar and pestle is added 2.00 g decolorized THCA powder. Targeting a sample that is 7% terpenes by mass, to the pile of powder is added 151 mg (approx. 178 microliters) of Tropical Trainwreck terpene blend dropwise. The components are lightly mixed with a spatula, then compounded together with the mortar and pestle yielding a relatively hard, sticky paste.

The contents of the mortar and any product adhering to the pestle are scraped onto a 16.times.24" sheet of parchment paper. The parchment paper is folded in half, to contain the product within it as an 'envelope.'

The product, contained within parchment paper, is then melted by heating on a hotplate preheated to 140-200 C for 2-10 seconds, or until it begins to melt. The parchment is quickly flipped and the product is heated again for the same period until the product is completely melted. The parchment containing the melted product is quickly set on a hard, flat surface and the product is rolled flat between the parchment paper using a rolling pin or other cylindrical roller, to form a thin sheet of product. Once rolled flat, the product is allowed to cool to room temperature and solidity.

In flatness embodiments, the product that needs to be flattened, can be flattened with a rolling pin, with clamp press, and so on, can have the following thicknesses. The thickness can be that measured at the approximate center of the flattened product, or the thickness can be the average of the thickness measured at twelve different equally spaced positions on the flattened product.

Whatever the method used for measuring thickness, the thickness can be 0.2 mm, 0.4 mm, 0.6 mm, 0.8 mm, 1 mm, 2 mm, 4 mm, 6 mm, 8 mm, 10 mm (1 cm), 1.5 cm, 2.0 cm, 2.5 cm, 3.0 cm, 3.5 cm, 4.0 cm, 4.5 cm, 5 cm, 6 cm, 7 cm, 8 cm, 9 cm, 10 cm, 15 cm, 20 cm, 30 cm, 40 cm, and so on. Also, the thickness can be about 0.2 mm, about 0.4 mm, about 0.6 mm, about 0.8 mm, about 1 mm, about 2 mm, about 4 mm, about 6 mm, about 8 mm, about 10 mm (about 1 cm) about 1.5 cm, about 2.0 cm, about 2.5 cm, about 3.0 cm, about 3.5 cm, about 4.0 cm, about 4.5 cm, about 5 cm, about 6 cm, about 7 cm, about 8 cm, about 9 cm, about 10 cm, about 15 cm, about 20 cm, about 30 cm, about 40 cm, and so on. In other thickness embodiments, the thickness can take the form of a range between any two or more adjacent numbers, that is, in the above lists of numbers.

The sheets of parchment are carefully opened to reveal the thin sheet of product, adherent to one side of the parchment envelope. The semi-solid product is then pooled by folding the product over onto itself causing it to cohere, then carefully separating the product from one of the two sheets of parchment.

After repeated folding, the product is now a much thicker 'slab.' As above, this slab is again placed between the opposing sheets of a sheet of parchment folded in half. The slab is again melted on a hot plate or griddle until made liquid, then again rolled flat into a large sheet, and allowed to cool to room temperature.

The product is again pooled into a thicker slab, and the process is repeated once more for a total of three melting, rolling and mixing repetitions.

After the third mixing event, the sheet of protoshatter may be trans erred to storage or packaging for sale. At this stage, the photoshatter can be briefly warmed with a heat:gun, causing it to melt—or "puddle"—into a visually appealing, transparent, glassy product.

DAC Method. To a 50 mL (75 #) DAC cup is added 13.9 grams decolorized THCA powder. To make a product loaded at 6% terpenes, 1.04 mL Berry GDP (880 mg) terpene blend is added dropwise. The cup is capped tightly and allowed to cool to −30 C in a freezer.

After 30 minutes of cooling, the contents of the cup are mixed in the DAC mixer (80 s, 2750 rpm) resulting in formation of a red, hard paste.

The paste is scraped from the DAC cup onto a sheet of parchment paper. The paper is folded in half to contain the product. The packet is then melted on a hotplate heated to 140-200 C for 2-10 seconds a side, then transferred to a hard flat surface and rolled into a flat sheet between the two pieces of parchment using a rolling pin. After cooling to room temperature and hardening, the parchment envelope is carefully opened and the product formed into a thicker slab by repeated folding upon itself. The melting, rolling process is repeated to ensure homogeneity. Upon cooling, the product is removed from parchment paper and heated for three seconds it a heat gun, causing it to form a transparent glassy product. Yield is 14 g protoshatter.

Formulation from Crystalline THCA Powder

Solution-Phase Pre-formulation. Pre-formulation is used to make amorphous THCA powder from crystalline THCA powder and to dilute it with raw. This enables manual formulation using the methods above (Mortar and Pestle Method).

To a 500 mL 2-neck round bottom flask outfitted with funnel and overhead stirrer is added 38.9 raw distillate followed by 150 mL n-pentane. The contents of the flask are stirred to dissolve the distillate (approximately 30 minutes). To a 2 liter, 3-neck flask outfitted with overhead stirrer, septum and funnel is charged 111.0 grams crystalline THCA powder. 400 mL pentane is added and the flask stirred. After complete dissolution of the distillate, the pentane solution is transferred to the 2-liter flask. The 500 mL flask is washed with 150 mL additional pentane and this rinse is also transferred to the 2-liter flask. The flask is stirred to achieve complete dissolution of all contents (approximately 1 hour).

After 1 hour, the resulting THCA/distillate pentane solution is divided into two fractions (by mass) which are charged to two separate 3-liter round bottom flasks. Solvent is removed from both flasks by rotary evaporation yielding a voluminous, foamy off-white solid. The flask is transferred to a vacuum manifold and purged on high vacuum for 48 h to remove solvent.

Once the flasks have reached a constant mass (48 h), they are removed from high vacuum and scraped with laboratory spatulas to yield 246.5 g slightly off-white powder. The powder is stored under nitrogen. Following pre-formulation, the product is formulated into protoshatter using methods for amorphous THCA powder (Mortar and Pestle Method).

Solid Phase Pre-formulation and Syringe Pump Method. To a 50 mL DAC cup (75 #) is added 14.3 g crystalline THCA powder, 2.4 g raw distillate added. The cup is chilled to −30 C in a freezer (30 minutes). The cup is then submitted to mixing in the DAC speed mixer (40 seconds, 2750 rpm) yielding an off-white powder with small chunks. This freezing/mixing sequence is repeated until a homogeneous, fluffy, off-white powder is achieved. Yield of pre-formulated powder is 16.7 grams. Typically, a total of 2-3 mixing cycles are sufficient.

To the DAC cup as above, containing 16.7 g powder is added 1.48 mL (1.26 grams) Pineapple Super Silver Haze terpene blend to yield a 7% dispersion. 7.0 grams of this dispersion—a paste—is manually loaded into a 10 mL gas-tight glass syringe with 14G, 2" needle. The barrel of the syringe is wrapped with heat tape. The needle is wrapped with heat tape or threaded through a heated stainless steel bar with small bore.

The barrel of the syringe is heated to 50-80 C and the needle heated to 100-200 C. The exact parameters ideal for final formulation of protoshatter arc somewhat indeterminate and seem to vary depending on a variety of factors. The syringe barrel is heated to prewarm the paste and to lubricate the syringe. 55-60 C is ideal. The temperature of the needle directly affects the product form. At temperatures lower than ideal, a cloudy, paste-like product is produced.

The syringe pump is set to 0.5-2.0 mL/min and a sheet of parchment paper positioned under the needle outlet. The pump is activated, extruding protoshatter in long strings. After dispensing the whole syringe, the product on parchment is briefly warmed on a hotplate then pooled by folding over repeatedly. The slab of product is briefly heated with a heat gun on its surface to yield 6.7 grams protoshatter as a transparent amber glass.

The present invention is not to be limited by compositions, reagents, methods, diagnostics, laboratory data, and the like, of the present disclosure. Also, the present invention is not be limited by any preferred embodiments that are disclosed herein.

What is claimed is:

1. A method of purifying cannabinoid acids, comprising:
   (a) preparing a plant extract comprising cannabinoid acids,
   (b) isolating the cannabinoid acids from the plant extract in the presence of a base consisting of lithium carbonate using an extraction process.

2. The method of claim 1, wherein the plant extract is *cannabis* or hemp plant extract.

3. The method of claim 1, further comprising crystallizing one or more of the isolated cannabinoid acids.

4. The method of claim 3 wherein the isolated cannabinoid acids are in amorphous form.

* * * * *